US011191434B2

(12) United States Patent
Adamson et al.

(10) Patent No.: US 11,191,434 B2
(45) Date of Patent: *Dec. 7, 2021

(54) SYSTEMS AND METHODS FOR SWEPT-SOURCE OPTICAL COHERENCE TOMOGRAPHIC VIBROGRAPHY

(71) Applicant: AUDIOPTICS MEDICAL INCORPORATED, Halifax (CA)

(72) Inventors: Robert Adamson, Halifax (CA); Daniel MacDougall, Dartmouth (CA); Manohar Bance, Cambridge (GB); Jeremy Brown, Halifax (CA)

(73) Assignee: AUDIOPTICS MEDICAL INCORPORATED, Halifax (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/938,285

(22) Filed: Jul. 24, 2020

(65) Prior Publication Data

US 2021/0007605 A1 Jan. 14, 2021

Related U.S. Application Data

(63) Continuation of application No. 15/758,026, filed as application No. PCT/CA2016/051199 on Oct. 14, 2016, now Pat. No. 10,729,327.

(Continued)

(51) Int. Cl.
*A61B 5/00* (2006.01)
*A61B 5/12* (2006.01)
(Continued)

(52) U.S. Cl.
CPC .......... *A61B 5/0066* (2013.01); *A61B 5/0051* (2013.01); *A61B 5/12* (2013.01);
(Continued)

(58) Field of Classification Search
CPC . G01B 9/02091; A61B 5/0051; A61B 5/0066; A61B 5/0073; A61B 5/0097;
(Continued)

(56) References Cited

U.S. PATENT DOCUMENTS

| 10,729,327 B2* | 8/2020 | Adamson | G01N 29/0672 |
| 2011/0174078 A1* | 7/2011 | Chinn | G01S 7/497 |
| | | | 73/657 |

(Continued)

OTHER PUBLICATIONS

Park et al. "Phase-sensitive optical coherence tomography using an Vernier-tuned distributed Bragg reflector swept laser in the mouse middle ear". Optics Letters, vol. 39, No. 21. pp. 6233-6236, Nov. 1, 2014. (Year: 2014).*

*Primary Examiner* — Michael A Lyons
(74) *Attorney, Agent, or Firm* — Hill & Schumacher

(57) ABSTRACT

Systems and methods are provided for performing OCT vibrography based on the synchronization of components of the OCT vibrography system. An A-scan trigger is employed to synchronize the operation of the scanning subsystem that scans the sample beam and an acoustic stimulus source that generates an acoustic stimulus for vibrographic measurements. The acoustic stimulus source is controlled such that when the scanning subsystem dwells on an imaging line selected for vibrography measurements, the acoustic stimulus is generated over a plurality of A-scans and the phase of the acoustic stimulus is locked to the A-scan trigger, such that the phase of the acoustic stimulus is incrementally modified with each A-scan. The accumulation of the acoustic phase is therefore synchronized to the A-scan trigger. The synchronization, providing synchronized acoustic phase evolution during each acoustic phase waveform cycle, permits the use of the OCT vibrography system for simultaneous anatomical and functional imaging.

19 Claims, 6 Drawing Sheets

Related U.S. Application Data

(60) Provisional application No. 62/242,597, filed on Oct. 16, 2015.

(51) Int. Cl.
    *G01N 29/06*     (2006.01)
    *G01N 29/24*     (2006.01)
    *G01B 9/02*     (2006.01)

(52) U.S. Cl.
    CPC ........ *A61B 5/7285* (2013.01); *G01B 9/02091* (2013.01); *G01N 29/0672* (2013.01); *G01N 29/2418* (2013.01); *A61B 5/0073* (2013.01); *A61B 5/0097* (2013.01)

(58) Field of Classification Search
    CPC .... A61B 5/12; A61B 5/7285; G01N 29/0672; G01N 29/2418
    See application file for complete search history.

(56) References Cited

U.S. PATENT DOCUMENTS

2013/0303910 A1* 11/2013 Hubbard .............. A61B 8/4461
    600/443
2015/0148654 A1* 5/2015 Whanwook ............ A61B 3/102
    600/407

\* cited by examiner

SYSTEMS AND METHODS FOR SWEPT-SOURCE OPTICAL COHERENCE TOMOGRAPHIC VIBROGRAPHY

CROSS-REFERENCE TO RELATED APPLICATION

This application is a Continuation application claiming the benefit of National Phase application Ser. No. 15/758,026, filed on Mar. 7, 2018, which claims the benefit of the international PCT Patent Application No. PCT/CA2016/051199, filed on Oct. 14, 2016, in English, which claims priority to U.S. Provisional Application No. 62/242,597, titled "SYSTEMS AND METHODS FOR SWEPT-SOURCE OCT" and filed on Oct. 16, 2015, the entire contents of which are incorporated herein by reference.

BACKGROUND

The present disclosure relates to optical coherence tomography systems and methods. More particularly, the present disclosure relates to optical coherence tomographic vibrography.

Optical coherence tomography (OCT) is an optical interferometric imaging technology that can produce depth-resolved images of sub-surface tissue structures. This is accomplished by taking a spatially coherent infrared light-source and splitting it between a reference beam and a sample probing beam. Light that is backscattered from structures within the sample are collected and interfered (combined) with the reference beam light in order to produce an interference pattern that, once processed, reveals the location of light-reflecting structures in the sample.

OCT measurements can be performed using various approaches, either in the time domain (TD-OCT) or in the frequency domain (e.g., Fourier transform approaches such as spectral domain [SD-OCT] or swept-source [SS-OCT]). The most recent of these to see significant advancements is SS-OCT, which is schematically illustrated in FIG. 1A. In SS-OCT, a wavelength-tunable laser 100 is used as the light source to probe the sample. By varying or "sweeping" the optical wavelength of light emanating from the laser, an interference pattern can be detected at many wavelengths and frequency analysis of the detected signal can be used to identify the z-position of a light-reflecting structure in a sample.

Referring to FIG. 1A, at each frequency, the laser fires through optical fiber 105 into a beam splitter 110 that splits the beam into reference 115 and sample 120 arms with a path length difference $\Delta D$. The beam of the reference arm follows fiber to its exit and then is reflected by a mirror 125, while the beam of the sample arm follows fiber to its exit and then contacts an area on the sample. Structures within the sample area may then reflect some of the beam back to the fiber. Both beams are added together at the beam splitter, photo-detected at photodetector 130, amplified by amplifier 135, and recorded in a computer (not shown). As optical frequency, $\nu$, is swept in time, oscillations are generated in the measured interferogram 140 with frequencies that are proportional to the path length differences in the two arms of the interferometer. A hypothetical depiction of such an interferogram is shown in the frequency domain (amplitude over time, 140), which is transformed into an A-line 145 (amplitude over distance, bottom right) using discrete Fourier analysis software running on the computer.

The interference pattern as measured by a photodiode contains oscillations in time whose frequencies are proportional to the depths of the reflectors in the sample. By occasional sampling of the interference patterns produced by an arbitrary wavelength sweep profile such that the sampling occurs at evenly spaced optical frequency intervals, or by sweeping the laser linearly in optical frequency and regularly sampling the interference pattern, etc., a reflectivity depth-profile of the sample along the beam path (called an "A-line" or "A-scan") can be obtained by taking the magnitude of the discrete-Fourier-transform (DFT) of the sampled interferograms. 2D (x by z, where z is defined along the axial direction of the beam) brightness mode images (called "B-mode" or "B-scan") can be constructed by scanning the beam across a field-of-view in x and stitching together adjacent A-Lines into an intensity map. Similarly, 3D B-mode volume renders of structures can be constructed from a stacked set of 2D B-mode images collected at various y positions. In medical diagnostics, B-mode images provide anatomical information, i.e. the ability to discern normal structures from pathological ones.

In Spectral Domain OCT (SD-OCT), shown in FIG. 1B, a beamsplitter 110 splits light from a broadband source 200 between a reference arm 115 and a sample arm 120 and the light reflected from the two arms is interfered at another beamsplitter (which, in some embodiments is just the first beamsplitter used again). The interfered light is dispersed using a dispersive optic 150 such as a dispersion grating and the spectrum of the signal is recorded using a photodetector array (line camera) 155. The spectrum 142 is the Fourier transform of the axial scan line 145 (A-line) giving the reflectivity of the tissue as a function of depth.

OCT can also be used to perform functional measurements in tissue. The magnitude of the DFT of the interferograms contains structural information about sub-surface reflectors, and the phase of the DFT contains dynamic information. Repeatedly acquired A-lines at the same x,y position of moving objects will contain phase differences that reflect the structures' motion in z. Phase-sensitive OCT (PS-OCT) systems derive additional image contrast from this phase information and can quantify dynamics, and are often referred to as Doppler Optical Coherence Tomography systems.

OCT has been applied to imaging the human tympanic membrane and middle ear. It has been shown that anatomical structures within the middle ear can be imaged using OCT; that tympanic membrane can be imaged in patients using OCT; and that PS-OCT can be used to perform functional imaging in the human middle ear by measuring the vibration of middle ear structures in response to sound. To date, the basic approach that has been taken to extracting magnitude-of-vibration information in non-real-time, benchtop PS-OCT relies on an acoustic stimulus that is applied to the ear; the acoustic frequency phase variations are then collected over many consecutive complete acoustic cycles and analyzed using Fourier analysis.

In order for meaningful information to be extracted from the changes in phase of the sampled interferograms, PS-OCT requires a high degree of phase stability. As such, performing PS-OCT in the time domain is difficult to implement and is incompatible with real-time imaging. PS-OCT is very compatible with SD-OCT as its lack of moving-parts and tuning mechanisms inherently provide very high wavelength repeatability, however "PS-SD-OCT" has been limited in scanning range due to complex-conjugate ambiguity and sensitivity-roll-off, making it less-attractive for use in imaging applications requiring more than a few millimeters of scanning range such as middle ear imaging. An important requirement for interferometric phase stability in SD-OCT and SS-OCT is wavelength-repeatability.

The recent availability of tunable lasers with long-coherence lengths has made SS-OCT a preferred approach for long-range imaging in the human middle ear. However, conventional tunable lasers used for SS-OCT (e.g., external cavity lasers tuned with, for example, polygon mirrors) suffer from a number of limitations. They exhibit phase instability owing to non-repeatability in mechanical tuning mechanisms. They suffer from electronic timing jitter due to the difficulty in adequately synchronizing laser sweeps with mechanical mirror positions and so require either a phase-reference reflector to be placed within the image, or for synchronization pulses to be generated by optical means. There remains a need to develop systems and methods that would allow for phase-sensitive OCT.

SUMMARY

Systems and methods are provided for performing OCT vibrography based on the synchronization of components of the OCT vibrography system. An A-scan trigger is employed to synchronize the operation of the scanning subsystem that scans the sample beam and an acoustic stimulus source that generates an acoustic stimulus for vibrographic measurements. The acoustic stimulus source is controlled such that when the scanning subsystem dwells on an imaging line selected for vibrography measurements, the acoustic stimulus is generated over a plurality of A-scans and the phase of the acoustic stimulus is locked to the A-scan trigger, such that the phase of the acoustic stimulus is incrementally modified with each A-scan. The accumulation of the acoustic phase is therefore synchronized to the A-scan trigger. The synchronization, providing synchronized acoustic phase evolution during each acoustic phase waveform cycle, permits the use of the OCT vibrography system for simultaneous anatomical and functional imaging.

Accordingly, in one aspect, there is provided an optical coherence tomographic vibrography system, the system comprising:
an optical coherence tomography subsystem comprising:
  a light source;
  an interferometer in optical communication with said light source, wherein said interferometer is configured to generate a sample beam and a reference beam; and
  a detector in optical communication with said interferometer for detecting the interfered reference beam and scattered light;
a scanning subsystem for scanning the sample beam onto an object within a field of view, wherein said interferometer is configured to interfere the reference beam with scattered laser light that is scattered from the object;
an acoustic stimulus source for generating an acoustic stimulus and directing the acoustic stimulus onto the object, such that the acoustic stimulus generates vibrations within the field of view of said scanning subsystem; and
control and processing circuitry operatively coupled to said optical coherence tomography subsystem, said scanning subsystem, said acoustic stimulus source, said control and processing circuitry comprising a processor and a memory, wherein the processor is configured to execute instructions stored in the memory for performing the steps of:
  (a) synchronizing said scanning subsystem with an A-scan trigger associated with said optical coherence tomography subsystem, such that the sample beam is scanned according to a plurality of image lines, and such that at least one A-scan is performed for each image line;
  (b) while performing step (a), controlling said scanning subsystem and said acoustic stimulus source such that, at one or more selected image lines that are selected for performing vibrography measurement, said scanning subsystem dwells for a time duration corresponding to a plurality of A-scans, and the acoustic stimulus is generated and phase-locked to the A-scan trigger, such that the phase of the acoustic stimulus is synchronously and incrementally modified with each A-scan of the plurality of A-scans, and such that the accumulation of acoustic phase during each selected image line is controlled according to the A-scan trigger; and
  (c) sampling signals detected by said detector, thereby obtaining sampled interferograms;
  (d) processing the sampled interferograms from the plurality of image lines to generate a B-mode image;
  (e) processing the sampled interferograms from the selected image lines to generate functional vibrography measures;
  (f) repeating steps (a)-(e) one or more times, thereby dynamically generating a series of B-mode image frames and a series of functional vibrography measures, such that the generation of the B-mode images is interleaved with the generation of the functional vibrography measures.

In another aspect, there is provided a method of synchronizing the operation of an optical coherence tomographic vibrography system, the optical coherence tomographic vibrography system comprising:
an optical coherence tomography subsystem comprising:
  a light source;
  an interferometer in optical communication with the light source, wherein the interferometer is configured to generate a sample beam and a reference beam; and
  a detector in optical communication with the interferometer for detecting the interfered reference beam and scattered light;
a scanning subsystem for scanning the sample beam onto an object within a field of view, wherein the interferometer is configured to interfere the reference beam with scattered laser light that is scattered from the object; and
an acoustic stimulus source for generating an acoustic stimulus and directing the acoustic stimulus onto the object, such that the acoustic stimulus generates vibrations within the field of view of the scanning subsystem;
the method comprising:
  (a) synchronizing the scanning subsystem with an A-scan trigger associated with the optical coherence tomography subsystem, such that the sample beam is scanned according to a plurality of image lines, and such that at least one A-scan is performed for each image line;
  (b) while performing step (a), controlling the scanning subsystem and the acoustic stimulus source such that, at one or more selected image lines that are selected for performing vibrography measurement, the scanning subsystem dwells for a time duration corresponding to a plurality of A-scans, and the acoustic stimulus is generated and phase-locked to the A-scan trigger, such that the phase of the acoustic stimulus is synchronously and incrementally modified with each A-scan of the plurality of A-scans, and such that the accumulation of acoustic phase during each selected image line is controlled according to the A-scan trigger;

(c) sampling signals detected by the detector, thereby obtaining sampled interferograms;

(d) processing the sampled interferograms from the plurality of image lines to generate a B-mode image;

(e) processing the sampled interferograms from the selected image lines to generate functional vibrography measures;

(f) repeating steps (a)-(e) one or more times, thereby dynamically generating a series of B-mode image frames and a series of functional vibrography measures, such that the generation of the B-mode images is interleaved with the generation of the functional vibrography measures.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
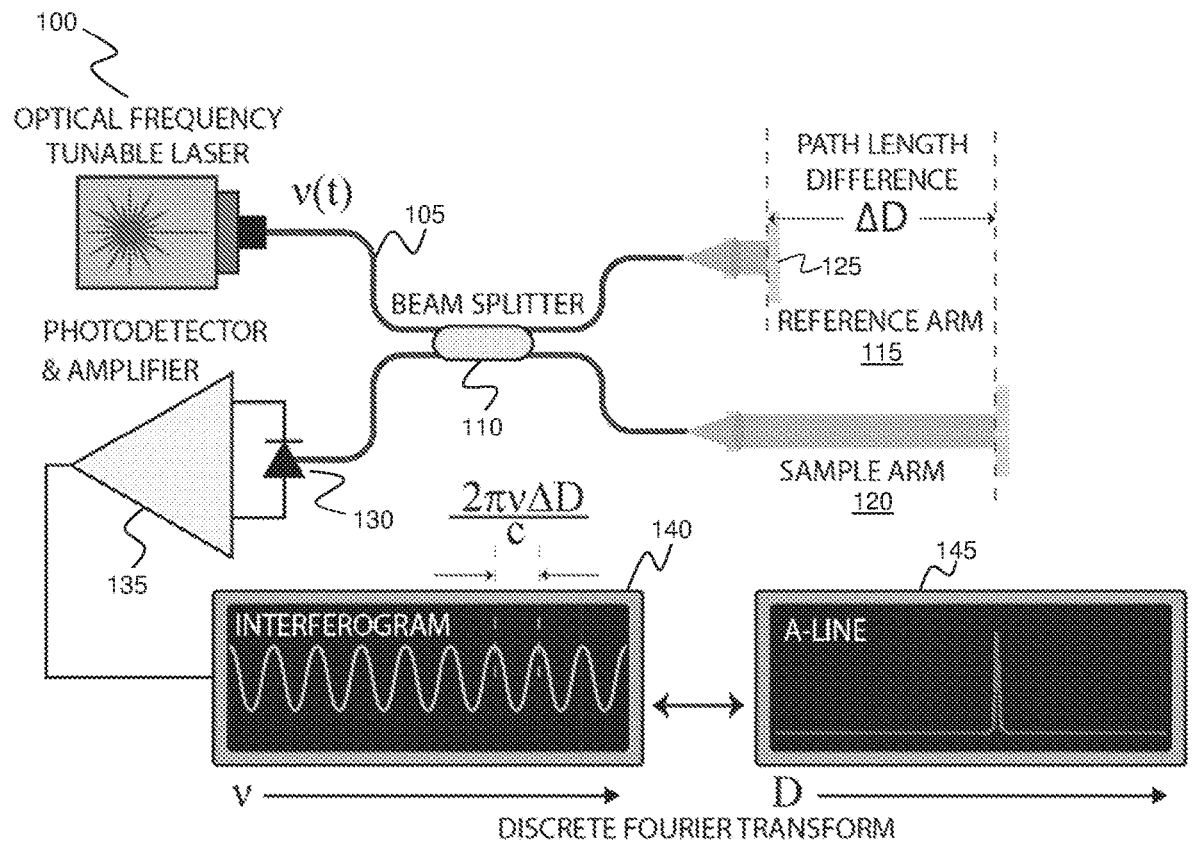
FIG. 1A illustrates a conventional swept-source optical coherence tomography (SS-OCT) system.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Described herein are systems and methods for performing phase-sensitive OCT vibrography. According to various example embodiments of the present disclosure, an optical coherence tomographic (OCT) vibrography system (also referred to herein as a phase-sensitive OCT system) provides an A-scan trigger, which is used for synchronization during vibrographic measurements. The A-scan trigger is employed to synchronize the operation of the scanning subsystem that scans the sample beam across an imaging field of view and an acoustic stimulus source that generates an acoustic stimulus for vibrographic measurements. The acoustic stimulus source is controlled such that when the scanning subsystem dwells on an imaging line that is selected for vibrography measurements, the acoustic stimulus is generated over a plurality of A-scans, where the phase of the acoustic stimulus is locked to the A-scan trigger, such that the phase of the acoustic stimulus is incrementally modified with each A-scan. As a result, the accumulation of the acoustic phase is controlled and synchronized to the A-scan trigger. Such synchronization with controlled acoustic phase evolution during each acoustic phase waveform cycle permits the use of the OCT vibrography system for simultaneous anatomical and functional imaging.

The system thus synchronizes the acquisition of samples of the interferograms, the scanning of the sample beam across the field of view being imaged, and the generation of acoustic stimuli used to excite the structures for diagnostic vibrography investigation. Furthermore, as described in detail below, the example systems and methods disclosed herein may be employed for the interleaving of real-time B-mode imaging with dynamic vibration measurements, which makes them well suited for use in real-time clinical diagnostic and therapeutic procedures.

In some example embodiments, the OCT subsystem is a swept source subsystem (SS-OCT), while in other example embodiments, the OCT subsystem is a spectral-domain OCT (SD-OCT) subsystem. For example, in some example embodiments, the OCT system of the OCT vibrography system is a swept-source OCT subsystem that employs an akinetic laser, such as a semiconductor-based Vernier cavity tuned laser. The akinetic laser provides exceptional phase repeatability, obviating the need for phase correction present in previously known OCT systems and simultaneously providing excellent interferometric phase-stability and long coherence length (desirable for long scanning range).

Such akinetic lasers do not need to be governed by external timing circuitry, and instead provide external timing for synchronizing of the system components. An akinetic laser provides synchronization signals for interfacing with acquisition cards based on the laser sample clock, and a sweep trigger (which may be derived by from the sample clock). The sample clock of the akinetic laser and the sweep trigger may therefore be employed so that interferogram sampling is well synchronized with laser-sweeping. Furthermore, the sweep trigger may be employed to synchronize the timing of laser frequency sweeping, the scanning of the sample beam across the field of view, and the generation and phase control of an acoustic stimulus, thereby permitting the dynamic and interleaved generation of B-mode imaging and the determination of functional vibrographic measures. Such a system provides the benefit of low-jitter synchronization, which, when combined with the phase-stability of an akinetic laser, allows for the simultaneous B-mode and functional imaging at real-time rates.

As described below, in some example embodiments, the systems and methods disclosed herein may be employed for otological procedures, such as the simultaneous anatomical and functional imaging of the human middle ear. However, it will be understood that the systems and methods described herein may be employed for a wide range of applications, including, but not limited to, medical diagnostic procedures.

Figure 2:
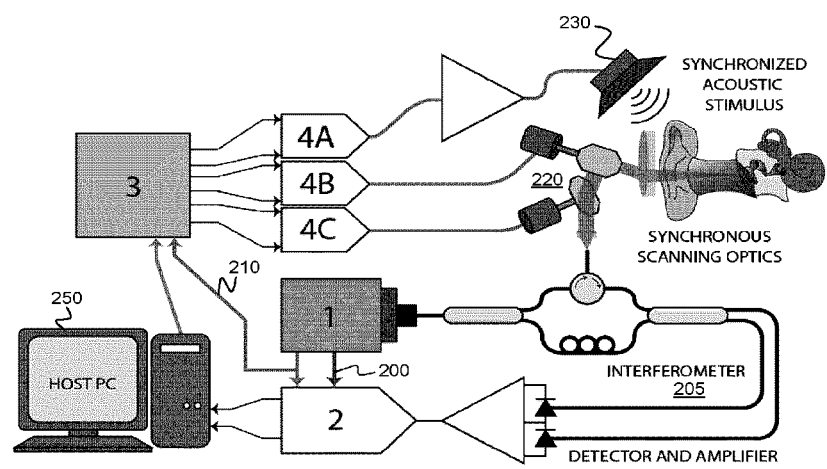
FIG. 2 shows an example embodiment of a SS-OCT vibrography system.

Referring now to FIG. 2, an example OCT vibrography system is shown that employs a swept-source akinetic laser 1, such as the SLE-101E akinetic laser from Insight Photonics Solutions, which provides a sweep frequency of 100 kHz and a fiber-based interferometer 205. The swept source laser 1 provides a sample clock 200 and a sweep trigger 210, where the sweep trigger 210 signals the beginning of each new laser sweep (each A-scan event corresponding to an acquired interferogram). The sweep trigger 210 may be derived from the sample clock 200. The sample clock 200 and sweep trigger 210 supply timing signals to other clocked and temporally synchronized components of the OCT vibrography system. The akinetic laser thus acts as the timing master to other system components, which themselves act as timing-slaves.

As shown in FIG. 2, the sample clock 200 and the sweep trigger 210 are provided to the data acquisition card 2 (e.g., ATS9351, 12-bit, 500 MHz PCIE digitizer, Alazar Technologies) to synchronize laser sweeping and data acquisition. The sweep trigger 210 is also used to clock internal functions of a field-programmable-gate-array 3 (e.g., MachXO2-7000HE, Lattice Semiconductor) that, through digital-to-analog converters 4 (DAC), respectively control the scanning optics 220 and the acoustic stimulus source 230 that generates an acoustic stimulus signal for excitation of the middle ear. In the present example embodiment, a digital synthesis approach may be employed to generate the scanning signals and acoustic signals. In the example implementation shown in FIG. 2, a computer 250 is employed to send control signals to components of the system, but the synchronization the optical beam scanning and the phase of the acoustic stimulus is determined by the sweep trigger.

The use of the single clock generated by the akinetic laser to synchronize the scanning subsystem 220 and the acoustic stimulus source 230 provides the advantage of synchronously controlling the phase of the acoustic stimulus during optical scanning. In the present example embodiment shown in FIG. 2, a synchronized acoustic stimulus signal is generated by the FPGA by incrementing a counter on the rising edge of each clock cycle (i.e., on each laser sweep). This counter acts as a phase accumulator and is used to step though a lookup table containing the values of a sinusoid of a particular acoustic frequency. On each clock edge, the FPGA updates the value of a digital-to-analog converter 4A (e.g., DAC900E, Texas Instruments) that drives an audio amplifier and speaker used to excite vibrations in the sample.

Two synchronized lateral digital scanning signals (one for horizontal scanning, and one for vertical scanning) are also generated by the FPGA by incrementing a counter on the rising edge of the each laser sweep clock cycle (i.e. In order to count laser sweeps). Once the desired number of laser sweeps for a particular scan configuration (image line) have completed, the scan mirror position is incremented by a chosen step size and the laser sweep counting starts over. This process is repeated once for every line in the image. Once the desired number of steps have been made (i.e. the number of lines in the image), the signal is reset to a chosen initial value and the lateral scan procedure starts over. The FPGA updates the values of two digital-to-analog converters 4B and 4C (e.g., DAC900E, Texas Instruments) that respectively trigger mirror drivers (shown as cylinders in FIG. 2) to drive the horizontal and vertical scanning optics/mirrors (shown as polygons in FIG. 2, mounted to their respective driver). In one example embodiment, there are two mirror drivers, each of which drive a mirror.

It is to be understood that while FIG. 2 shows a mirror-based scanning subsystem 220, in other example embodiments, one or more of the mirrors may be replaced by other scanning elements. Non-limiting examples of non-mirror based scanning elements include acousto-optic deflectors, electro-optic deflectors, liquid crystal spatial light modulators, and photorefractive scanners.

In some example implementations, the systems and methods of the present disclosure may be employed for otological vibrographic measurements. When an acoustic tone is presented to the ear, the middle ear structures (the eardrum and ossicles) are set into periodic motion at the acoustic frequency as they conduct sound energy to the inner ear. When the vibrating structures are imaged with PS-SS-OCT, phase variations in the interferometric signal appear at the acoustic frequency as well. While the audible range of acoustic frequencies is typically cited as 20 Hz-20 kHz, the most useful diagnostic range of acoustic frequencies for otology is below ≈2 kHz (period >500 µs) where the response of the ossicles is quasi-static and predictable.

For real-time imaging (≈20 frames-per-second, FPS) with diagnostic images containing several hundred image lines, a practical limit is approached where the available acquisition time per image-line, per image-frame, approaches the duration of the acoustic period of motion. This time limitation prevents effective use of simple Fourier analysis due to insufficient spectral resolution, as well as other simple forms of multi-acoustic-cycle-averaging.

Some example embodiments of the present disclosure provide solutions to this problem by averaging vibrographic measurements over multiple image frames, thereby permitting the display of B-mode image frames at sufficiently high frame rates for real-time imaging (e.g. >=20 FPS), while dynamic vibrographic measures that are averaged over multiple image frames.

Figure 3A:
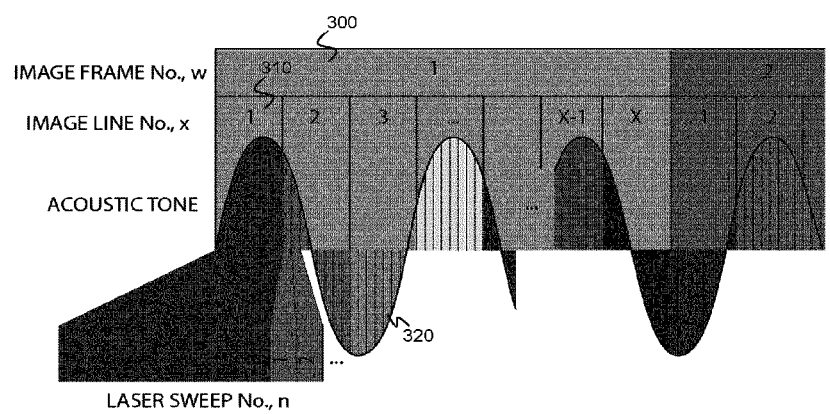
FIG. 3A illustrates an example method involving the synchronous control of the evolution of the phase of the acoustic stimulus while controlling the scanning of the optical beam among multiple image lines, in which vibrography measures obtained for each image line are averaged among multiple image frames.

FIG. 3A provides an example embodiment in which multi-frame averaging is employed to interleave B-mode imaging with the generation of vibrographic measures, based on the use of the sweep trigger to control and synchronization of the phase evolution of the acoustic stimulus among multiple image frames. Each image frame 300, indexed by w, is composed of X image lines 310, indexed by x. Each image line contained Y pixels 320, indexed by y, and is calculated from N rapidly acquired interferograms corresponding to N laser sweeps, indexed by n. FIG. 3A also highlights a key difference between the present system and the more common application of PS-OCT to real-time fluid flow measurements (e.g. in angiography), where unidirectional flow produces a constant and repeatable phase-shift between all adjacent A-scans, making averaging trivial even at real-time rates. In vibrography, however, since the motions are sinusoidal, the magnitude and sign of phase shifts between adjacent A-scans varies continuously.

In the present example embodiment, by ensuring that the acoustic excitation remains phase-locked to the laser sweeps, the accumulation of acoustic phase during and between consecutive image frames can be controlled, predicted, and accounted-for, to allow averaging that makes interleaving of Doppler and B-mode acquisition possible. Without such phase-locking, even relatively slow-phase drifts between the acoustic stimulus and the laser sweeping would tend to average away the vibrational information.

In one example implementation, signal processing can be performed according to the following mathematical relations. Given the desired acoustic frequency, $f_{acoustic}$, and a laser sweep rate, $f_{sweep}$, the amount of acoustic phase accumulated during any laser sweep, n, of any image line, x, of any image frame, w, is constant and given by the expression:

$$\Delta\phi_{w,x,n} = \Delta\phi = 2\pi\frac{f_{acoustic}}{f_{sweep}}$$

Therefore the total amount of acoustic phase accumulated during any complete image line is given by $N \times \Delta\phi$, and that accumulated during any complete image frame is given by $N \times X \times \Delta\phi$. It follows that the total acoustic phase accumulated since reference point $(w,x,n)=(0,0,0)$ at laser sweep n, of image line x, in image frame w can be calculated as:

$$\phi_{w,x,n} = \Delta\phi \times [n + x \times n + w \times X \times N]$$

It is therefore expected that the measured optical phase (i.e. the phase of the DFT of the interferogram) of a vibrating reflector located at pixel y of image line x, to be described by:

$$\psi_{w,x,y,n} = \frac{4\pi A_{x,y}}{\lambda_0}\sin(\phi_{w,x,n} + \phi_{x,y}) + \psi_{x,y} + \psi_{noise}$$

Where $A_{x,y}$ is the amplitude of acoustic vibration, $\lambda_0$ is the center optical wavelength, $\phi_{x,y}$ is the acoustic phase shift of the reflector resulting from its dynamic response characteristics, $\psi_{x,y}$ is the optical phase that would be measured with no acoustic stimulus present (i.e. a stationary sample), and $\psi_{noise}$ is the optical phase noise in the system owing to thermal drifts, mechanical noise, and wavelength repeatability in the laser.

$A_{x,y}$ and $\phi_{x,y}$ are both of diagnostic significance for middle ear structures and can be extracted from the measured phase data by calculating the cross-correlation of the measured signal with an in-phase and quadrature-phase acoustic sinusoid at the acoustic frequency. Formally, if W image frames worth of data to are employed to contribute to the estimation of $A_{x,y}$ and $\phi_{x,y}$, the following calculation can be performed $$A_{x,y}e^{j\phi_{x,y}} = \frac{\lambda_0}{2\pi} \times \frac{1}{N \times W} \sum_{w=0}^{W-1}\sum_{n=0}^{N-1} e^{j\phi_{w,x,n}}\psi_{w,x,y,n}$$

which is a cross correlation between the measured phase variations and the complex acoustic wave.

It is the synchronization of the timing components to the akinetic laser clock that allows this simple form of indexing to track acoustic phase changes, and makes the processing steps well suited to parallel processing on graphical processing units (GPUs) using, for instance, the Compute Unified Device Architecture (CUDA) framework.

It will be understood, however, that the systems and methods described herein need not be implemented according to the example hardware configurations described above and shown in FIG. 2. In an embodiment, other computer hardware may be employed as processing circuitry to perform the collection, synchronization, and analysis, in which processing circuitry, including at least one processor and memory, is operably connected to the optical coherence tomography subsystem to receive the A-scan trigger therefrom, and is configured such that the at least one processor is configured to execute instructions stored in the memory for performing the methods disclosed herein. In one example implementation, one or more GPUs are employed to perform the collection and analysis. In another implementation the processing may be performed on a CPU. In yet another implementation the processing may be performed on a FPGA in communication with a computer. In other implementations, data collection is performed by an FPGA or other programmable processor with an embedded analog-to-digital converter that is synchronized to the laser sweep trigger, wherein raw sampled data is digitally transferred to a host computer that performs the processing. In other implementations, data acquisition is performed by an FPGA or other programmable processor with an embedded analog-to-digital converter that is synchronized to the laser sweep trigger, wherein the sampled data is collected and partly or completely processed locally on embedded programmable hardware before transmission and completion of processing on a host computer.

The example methods described herein, in which the acoustic stimulus phase is locked and synchronized to the laser sweep trigger, are well suited when using akinetic lasers because of the characteristic way that linear sweeping over a broad bandwidth is achieved: through controlled mode-hopping in the akinetic swept-source architecture. The laser executes linear-in-frequency sweeps over a limited frequency range. When the end of that range is reached the laser undergoes a mode-hopping event. During this event the interferogram data is invalid and must be removed prior to line reconstruction. Fortunately, the mode hops are repeatable and deterministic across sweeps and so for a given laser calibration and set of sweep settings the invalid data can be identified. However, the presence of these invalid points and their dependence on calibration and sweep parameters means that a system synchronized to the laser sampling clock (or the "k-clock" in the language conventionally used for swept source lasers) results in a phase error that depends on the sweep settings and calibration. In an embodiment, synchronizing to the start of the sweep with an external FPGA avoids this phase error.

In the preceding example method that was described with reference to FIG. 3A, the vibrography measures obtained for each image line are averaged among multiple image frames, where the averaging process is interleaved with the display of B-mode image frames. In other example embodiments, the vibrographic measurements may be made for a subset of selected image lines. For example, vibrography measurements may be performed for a single selected image line, a pair of selected image lines, or a larger set of selected image lines. In some implementations, the scanning system may be controlled to dwell at a selected image line for a time duration that is permits that acquisition of sufficient samples to generate one or more vibrational measures without the need to perform averaging during subsequent image frames. According to such an implementation, the vibrography measures, which are associated with the set of selected image lines that are a subset of the full set of image lines used for B-mode imaging, may be generated and updated in real-time with the real-time B-mode images.

For example, in an example implementation in which a single image line is selected for performing vibrography measures, the scanning subsystem can be controlled such that the dwell time at the selected image line is sufficiently long to permit the acquisition of a sufficient number of interferograms for generating the vibrography measures with a suitable signal-to-noise ratio, such as a dwell time on the order of seconds, while rapidly scanning among the remainder of the image lines (the non-selected image lines), with a dwell time on the order of milliseconds, in order to collect interferograms suitable for generating B-mode image data.

In another example embodiment, the vibrography measures may be obtained at a subset of selected image lines, and where the vibrography measures for each selected image line are averaged among two or more image frames. Such an embodiment is beneficial in reducing the time required for vibrographic measurements via the selection of a subset of image lines for vibrographic analysis, while maintaining a higher frame rate (e.g. sufficiently high for real-time B-mode imaging) by permitting averaging of vibrographic measures among multiple image frames.

Figure 3B:
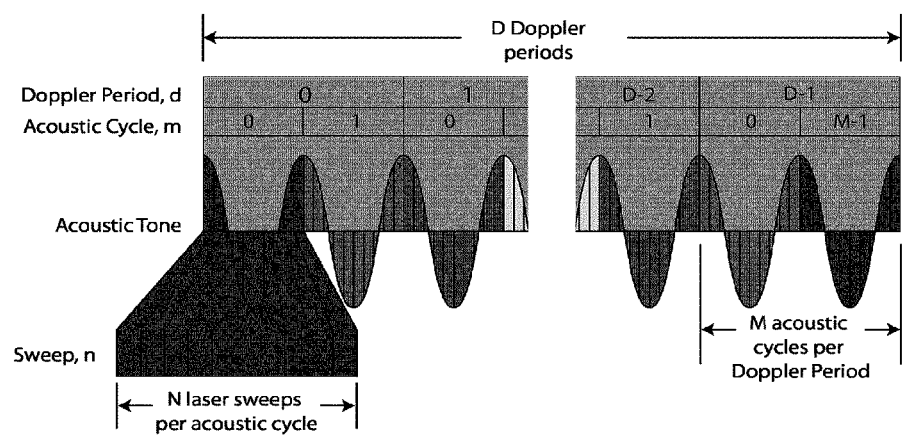
FIG. 3B illustrates an example method of processing sampled interferograms for the generation of vibrography measures, in which a plurality of acoustic cycles are generated per image line, and where the plurality of acoustic cycles are divided into groups of acoustic cycles, each group having one or more full acoustic cycles, and where the functional vibrography measures from each group of acoustic cycles are generated and averaged to provide averaged vibrography measures.

FIG. 3B illustrates an example method of processing sampled interferograms for the generation of vibrography measures. When acquiring functional vibrography data, a sequence of A-lines (i.e. the sequence of DFTs of the spectral interferograms) are grouped into D "Doppler periods", indexed by d, within each of which vibrographic information can be extracted. The duration of the Doppler period can be chosen such that, M cycles of the acoustic tone fit within it, indexed by m. According to such an example embodiment, a plurality of acoustic cycles are generated per image line, where the plurality of acoustic cycles are divided into groups of acoustic cycles (the Doppler periods), each group having one or more full acoustic cycles. As described below, the functional vibrography measures from each group of acoustic cycles can be separately generated and subsequently averaged to provide averaged vibrography measures in a computationally convenient manner.

With the system configured to generate an acoustic tone that corresponds to N laser sweeps in duration (acoustic period of N sweeps), the amount of acoustic phase accumulated per sweep is given by $$\Delta \phi = 2\pi \frac{f_a}{f_s} = \frac{2\pi}{N}$$

Where $f_a$ is the frequency of acoustic stimulus and $f_s$ is the laser sweep frequency. The number of sweeps that have occurred since time t=0 is given by n+mN+dMN, and so the total acoustic phase accumulation since t=0 can be easily be predicted by $$\phi_{nmd} = \frac{2\pi}{N}(n + mN + dMN)$$

In a non-limiting example case in which the OCT beam is not scanning, it is made to dwell at a single image line for the entire D Doppler periods. For a stimulated vibrating structure located at a depth such that it appears in pixel y of the A-line data, the optical phase measured at pixel y is expected to be described by $$\psi_{ynmd} = \frac{4\pi A_y}{\lambda_0} \sin(\phi_{nmd} + \phi_y) + \psi_y + \psi_{noise}$$

Where $A_y$ is the amplitude of the oscillatory displacement stimulated by the applied tone, $\lambda_0$ is the central wavelength of the OCT beam, $\phi_y$ is the acoustic phase shift of the structure resulting from its dynamic response characteristics, $\psi_y$ is the constant optical phase that would be measured at the structure if there were no oscillatory motion or measurement noise, and $\psi_{noise}$ is the optical phase noise in the system owing to thermal drifts, mechanical noise, and wavelength repeatability in the laser. $A_y$ and $\phi_y$ are the key vibrography parameter of interest. Within a single Doppler Period, an estimate of these parameters can be made by computing an appropriately scaled cross-correlation between the optical phase changes in time and the complex acoustic phasor.

$$\langle A_y e^{j\phi_y} \rangle = \frac{\lambda_0}{2\pi} \times \frac{1}{MN} \sum_{m=0}^{M-1} \sum_{n=0}^{N-1} e^{-j\phi_{nmd}} \psi_{ynmd}$$

Which can equivalently be thought of as a computation of the single coefficient of the M×N point DFT of the phase change within the Doppler Period that corresponds exactly the acoustic frequency of the stimulus. In order to gain SNR and achieve improved estimates of $A_y$ and $\phi_y$, averaging of the results from D Doppler periods can be performed as well $$\langle A_y e^{j\phi_y} \rangle = \frac{1}{D} \sum_d \frac{\lambda_0}{2\pi} \times \frac{1}{MN} \sum_{m=0}^{M-1} \sum_{n=0}^{N-1} e^{-j\phi_{nmd}} \psi_{ynmd}$$

$$\langle A_y e^{j\phi_y} \rangle = \frac{\lambda_0}{2\pi} \times \frac{1}{DMN} \sum_d \sum_{m=0}^{M-1} \sum_{n=0}^{N-1} e^{-jd_{nmd}} \psi_{ynmd}$$

Which can equivalently be thought of as a computation of the single coefficient of the D×M×N point DFT of the phase change at pixel y. There are several key advantages that this approach provides.

The preceding example method is beneficial in that the sum over d can be performed in any way one wishes to scan the sample. For example, If the OCT beam is allowed to dwell for long periods of time on a structure of interest, the sum over d can be carried out over consecutive Doppler periods. However, the interleaving of Doppler measurements with B-mode imaging can be implemented by summing Doppler periods that are separated by long periods of time (e.g. between consecutive image frames), wherein B-mode imaging could easily be performed. This allows tracking of the anatomy during Doppler measurements.

Another benefit of the present example method is that phase data need only be unwrapped within each Doppler period. The phase discontinuities that remain between adjacent Doppler periods or between Doppler periods separated by long times does not impact the end result of the calculation.

Yet another benefit of the present example method is that the cross correlation is well suited to parallel processing on a graphics processing unit (GPU), since the sums over N and M are easily separable, and because the individual Doppler periods can be processed independently from one another.

Figure 4:
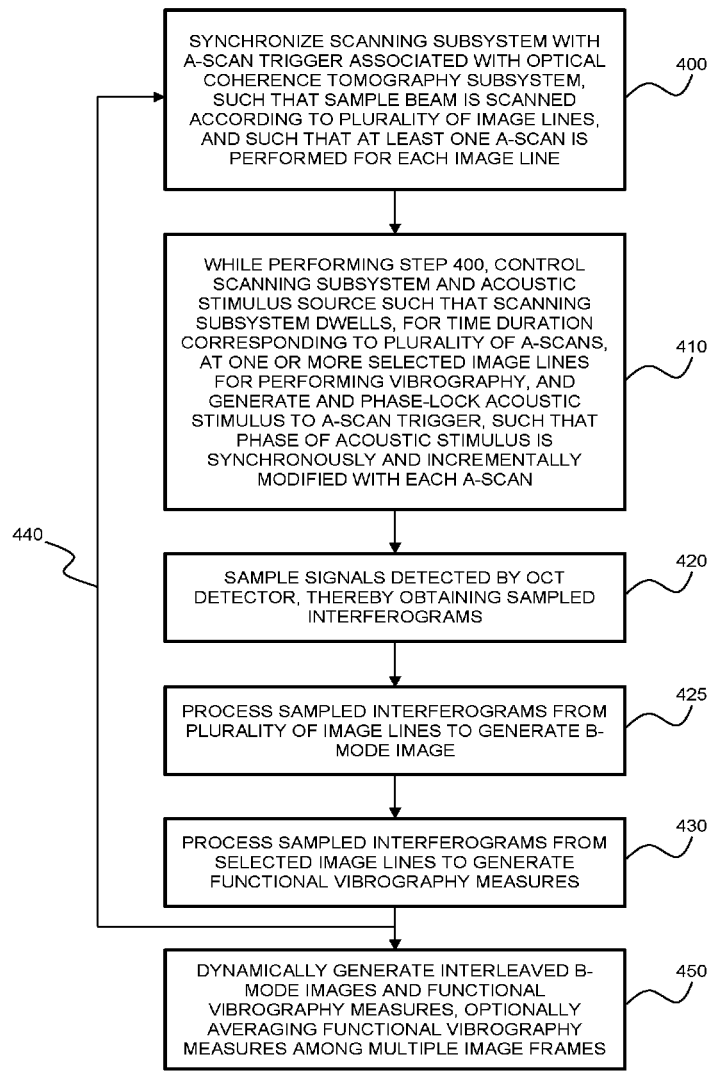
FIG. 4 is a flow chart providing an example method of performing optical coherence tomographic vibrography.

The methods described above are described in the flow chart provided in FIG. 4. In step 400, the scanning subsystem is synchronized with the A-scan trigger that is associated with the optical coherence tomography subsystem, such that sample beam is scanned according to plurality of image lines, and such that at least one a-scan is performed for each image line. The sample beam is thus scanned across a field of view and image data is collected for generating a B-mode image. However, as shown at 410, while performing step 400, the scanning system and the acoustic stimulus source are controlled such that the scanning subsystem dwells, for a time duration corresponding to plurality of a-scans, at one or more selected image lines for performing vibrography, and the acoustic stimulus is generated and phase-locked to the a-scan trigger, such that the phase of the acoustic stimulus is synchronously and incrementally modified with each a-scan. As shown at step 420, the signals detected by the OCT detector are synchronously sampled, thereby generating a set of interferograms. In step 425, the interferograms from the various image lines are processed to generate a B-mode image, while in step 430, the interferograms from the selected image lines are processed (e.g. cross-correlated with sinusoidal in-phase and quadrature waveforms at the acoustic frequency) to generate the functional vibrography measures. This process is repeated, as shown at step 440, thereby providing dynamically generated B-mode images, optionally at real-time frame rates, interleaved with dynamically generated functional vibrographic measures, as shown at step 450. The function vibrographic measures may be processed such that they are averaged among multiple image frames in order to achieve a desirable signal-to-noise ratio.

When vibrographic and B-mode imaging are to be interleaved, or whenever vibrographic measurement time must be limited, a subset of the full set of possible image lines can be used. Since the distribution of the vibration pattern of the eardrum varies slowly, and because the ossicles of the middle ear move as rigid bodies, very dense spatial sampling of the vibrational pattern is not generally required to provide useful functional information. In some implementations, single lines may be manually selected by the user to have Doppler measurements interleaved with B-mode imaging. Alternatively, the system could be configured to only perform vibrography measurements on a sparse grid within the field of view (i.e. separated by many images lines). The identification of the subset of image lines over which Doppler measurements are to be performed could also be fully or partially automated using image segmentation of the interleaved B-mode image by identifying and tracking the key anatomical structures of interest within the middle ear.

Since the collection of vibrography information takes longer than collection of information needed to form B-mode images, implementations that run in real time may employ the selecting of which lines out of a B-mode image or a volume will be have vibrography information acquired. This selection can be performed manually by an operator, or may be done by in an automated fashion by use of an algorithm that selects the line. For example, in the middle ear, vibration information is associated with anatomical structures, and so line selection for vibrometry is often performed by identifying and segmenting anatomical structures within the image volume. In some example implementations, structures are identified and segmented based on their anatomical location, such as their location within the middle ear volume. In other implementations structures are identified and segmented based on the phase and amplitude of the vibration. For example, all voxels in the same rigid structures (such as an ossicle) will have the same vibration phase, and so vibration phase can be used to segment out the rigid structure. In other example implementations, structures are identified and segmented based on their optical properties including one or more of backscatter intensity, speckle texture and birefringence. In other example implementations, structures are identified and segmented based on their shape.

Identification and segmentation may be implemented, for example, using one of more segmentation algorithms that are known in the art. Such algorithms may involve one or more of thresholding based on one or more of the properties described above, clustering, compression, histogramming, edge detection, region growing (e.g. through erosion and dilation methods), methods based on minimization of a cost function such as parametric methods, level set methods and marching methods, variational methods, graph partitioning methods, watershed methods, model-based methods such as those that rely on distortion of a template.

An example of an implementation that automatically selects the subset of lines would use a combination of edge detection and clustering techniques can be applied to extract the surfaces of reflective structures (e.g. the bony ossicles) and to distinguish them from air based on backscatter strength (i.e. whether or not you can see them in the image) and different structures would be identified by their spatial location within the image or within a 3D volume by correlation against an anatomical atlas. The main feature being used to segment structures is their location within the middle ear volume, relative to the easily identified eardrum and bony cochlear promontory. Other features that could be used are the phase and amplitude of the vibration (rigid structures will move rigidly), the optical properties of the tissue such as backscatter intensity, speckle texture, birefringence (i.e. to distinguish bone from muscle), and the shape of the structures.

In an example embodiment, additional compensation may be applied to remove predictable unwanted components of the phase signal that undesirably correlate with the complex acoustic wave.

In an example embodiment, unwanted correlation artefacts introduced by large amplitude low-frequency phase drifts may be minimized by subtracting the average phase of a subset or subsets of the measured optical phases. For example, if it is known that for physiological reasons a particular structure should not vibrate in response to the sound stimulus (e.g. the cochlear promontory for middle ear imaging), then its motion may be considered an artefact related to patient motion and may be subtracted from all structures in the image, resulting in an improved estimated of the vibration level of those structures that do vibrate.

Figure 1B:
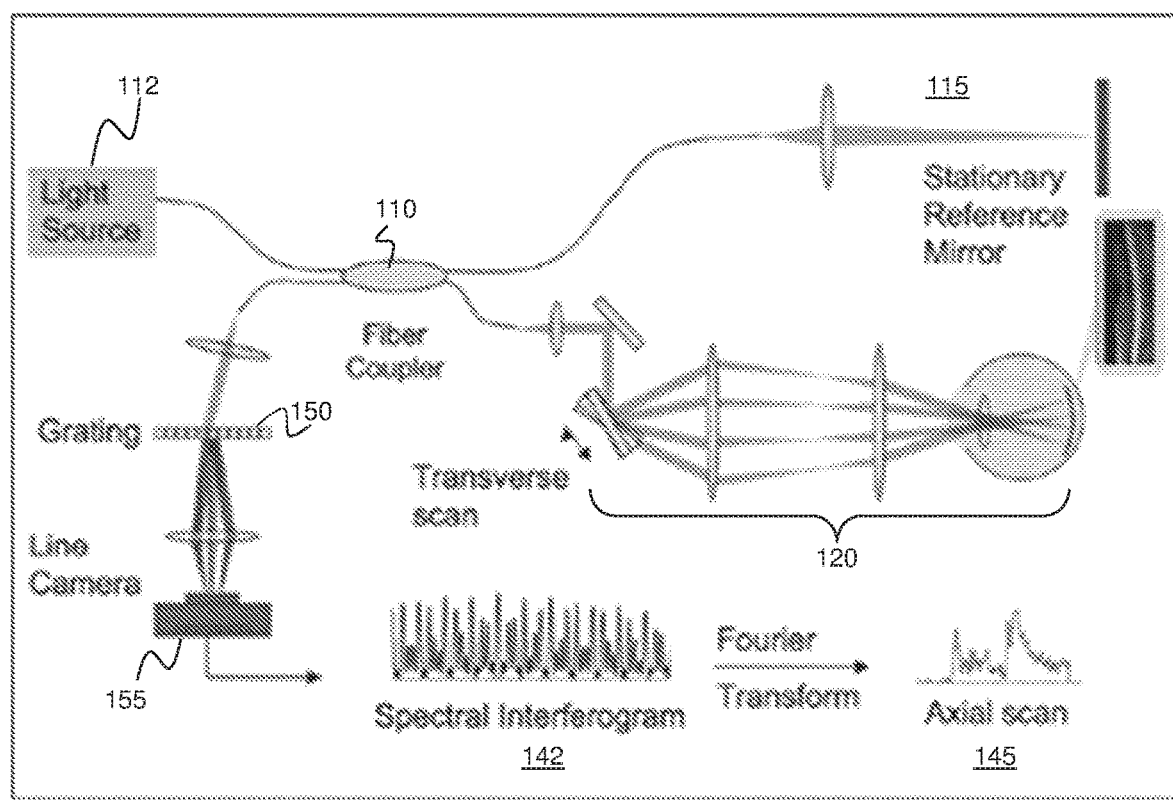
FIG. 1B illustrates a conventional spectral-domain optical coherence tomography (SD-OCT) system.

In some example embodiments, the methods and systems described above can be adapted to spectral domain optical coherence tomography (SD-OCT) vibrography. As described above with reference to FIG. 1B, SD-OCT systems direct the collected and interfered light onto a spectrometer and the intensity at discrete optical wavelengths is recorded by, for instance, a CMOS detector array, charge-coupled device (CCD) or photodiode array. In SD-OCT systems using this approach, the detector array signal is appropriately resampled to obtain measurements that are linearly spaced in optical frequency, and then Fourier transformed forming an A-scan signal. The phase of consecutive A-scans is multiplied by in-phase and quadrature sinusoids and averaged. The preceding example embodiments, described in the context of swept-source OCT vibrography, can be adapted to SD-OCT systems by employing the A-scan trigger, employed to trigger the acquisition of a spectrum from the detector array, in the place of the sweep trigger, such that the scanning subsystem and the acoustic stimulus subsystem are synchronized with the A-scan trigger.

It will be understood that the vibrographic measures may be generated as vibrographic images, or as non-image data. For example, one or more vibrographic measures may be generated based on the measurement at a single image line, or, for example, at a subset of image lines that correspond to different structures. Furthermore, although sinusoidal excitation provide magnitude and phase at each pixel, these could be used to construct more generic measures that may be of diagnostic importance or utility. For example, comparative measures, such as the ratio of umbo to stapes motion is may be a good indicator of otosclerosis, and this measure can be calculated using phase data as an input.

The following examples are presented to enable those skilled in the art to understand and to practice embodiments of the present disclosure. They should not be considered as a limitation on the scope of the disclosure, but merely as being illustrative and representative thereof.

EXAMPLES

Measurement of Quality of Synchronization using a Phantom

Figure 5A:
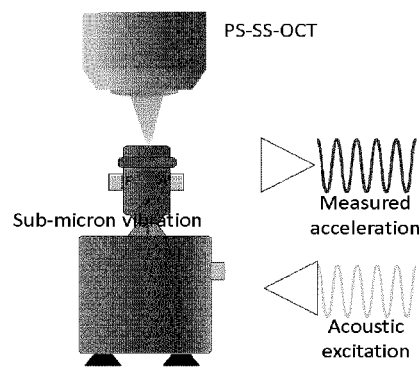
FIGS. 5A and 5B show (A) an experimental setup for measuring quality of synchronization, which was used to determine the vibrational noise floor in a particular setup, and the linearity of measurements; and (B) a graph demonstrating quality of synchronization of a PS-SS-OCT system.

The PS-SS-OCT (also sometimes referred to herein as Doppler swept-source OCT or phase sensitive Doppler swept-source OCT) system depicted in FIG. 2 and described above was tested in an experiment, the setup of which is depicted in FIG. 5A (OCT shown at top). The structure and vibrational response of a sample can be simultaneously acquired using such a system. The system included a laser with a sweep rate up to 100 kHz. For this experiment, the system included software and GPU hardware that enabled real-time collection and analysis as described above.

For the "sample" to be imaged, this experiment utilized a phantom (shown at middle of FIG. 5A) that had an acoustic frequency of excitation at approximately 2.2 kHz, generating sub-micron axial vibration when driven by an acoustic exciter (shown at bottom of FIG. 5A). An accelerometer (a calibrated Bruel and Kjaer 8001 impedance head) was attached to the phantom to compare the measured axial acceleration with that measured by the OCT system. Imaging was performed using 100% duty cycle laser sweeping (100 kHz). Real-time analysis was averaged over 0.5 s of vibration.

Figure 5B:
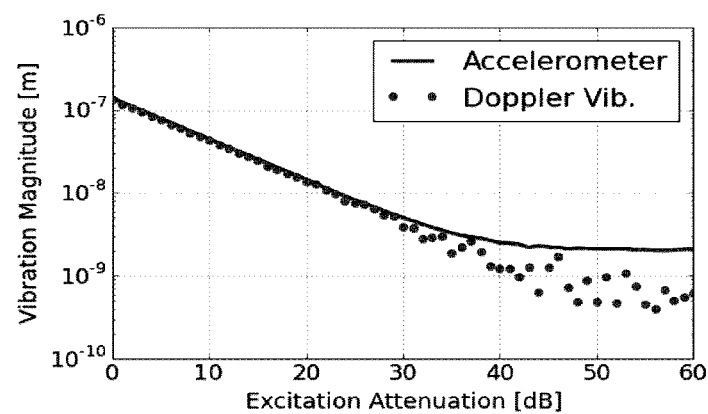

Results are plotted in FIG. 5B (dots representing the measurement of vibration by the Doppler swept-source OCT vs the solid line representing analogous measurement using the accelerometer). It can be seen that both methods perform equally down to below about 10 nm, and that the OCT system produces nanometer-level vibration precision across a broadly physiologically relevant and diagnostically useful range for imaging: 1 nm to 1000 nm.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. An optical coherence tomographic vibrography system, the system comprising:
  an optical coherence tomography subsystem comprising:
    a light source;
    an interferometer in optical communication with said light source, wherein said interferometer is configured to generate a sample beam and a reference beam; and
    a detector in optical communication with said interferometer;
  a scanning subsystem for scanning the sample beam onto an object within a field of view, wherein said interferometer is configured to interfere the reference beam with scattered laser light that is scattered from the object such that the interfered reference beam and scattered laser light are detected by said detector;
  an acoustic stimulus source for generating an acoustic stimulus and directing the acoustic stimulus onto the object, such that the acoustic stimulus generates vibrations within the field of view of said scanning subsystem; and
  control and processing circuitry operatively coupled to said optical coherence tomography subsystem, said scanning subsystem, said acoustic stimulus source, said control and processing circuitry comprising a processor and a memory, wherein the processor is configured to execute instructions stored in the memory for performing the steps of:
    (a) synchronizing said scanning subsystem with an A-scan trigger associated with said optical coherence tomography subsystem to scan the sample beam according to a plurality of scanning configurations;

(b) while performing step (a), performing the following steps for one or more selected scanning configuration that are selected for performing vibrography measurement:
controlling said scanning subsystem to maintain a scan configuration corresponding to the selected scanning configuration for a time duration corresponding to a plurality of A-scans; and
controlling said acoustic stimulus source to generate the acoustic stimulus with a waveform having a frequency that is less than a frequency of the A-scan trigger, the waveform being generated by synchronously incrementing the phase of the acoustic stimulus with each A-scan trigger, with each cycle of the waveform being associated with multiple A-scans, whereby the accumulation and evolution of the acoustic phase during each waveform cycle is controlled according to the A-scan trigger;
(c) sampling signals detected by said detector, thereby obtaining sampled interferograms; and
(d) processing the sampled interferograms from the selected scanning configuration to generate functional vibrography measures.

2. The system according to claim 1 wherein said optical coherence tomography subsystem is a swept-source optical coherence tomography subsystem, such that said light source is a swept-source laser that generates a sample clock, wherein the A-scan trigger is a sweep trigger that is generated from the sample clock, and wherein said control and processing circuitry is configured such that when performing step (c), the signals are sampled synchronously with the sample clock.

3. The system according to claim 2 wherein said swept-source laser is an akinetic swept source laser.

4. The system according to claim 1 wherein said optical coherence tomography subsystem is a spectral domain optical coherence tomography subsystem, such that said detector is a detector array in optical communication with a dispersive element.

5. The system according to claim 1 wherein said control and processing circuitry is configured such that the scanning configurations are associated with a set of image lines for generating an image frame, and wherein the functional vibrography measures generated from one or more consecutive image frames are averaged for each selected image line.

6. The system according to claim 5 wherein said control and processing circuitry is configured to control said scanning subsystem and said acoustic stimulus source such that less than one acoustic cycle is generated for each selected image line.

7. The system according to claim 1 wherein said control and processing circuitry is configured such that the scanning configurations are associated with a set of image lines for generating an image frame, and wherein said scanning subsystem and said acoustic stimulus source are controlled such that a plurality of full acoustic cycles are generated for each selected image line.

8. The system according to claim 7 wherein said control and processing circuitry is configured such that the functional vibrography measures corresponding to one or more consecutive image frames are averaged for each selected image line.

9. The system according to claim 7 wherein said control and processing circuitry is configured such that when performing step (d), for each selected image line, the plurality of acoustic cycles are divided into a plurality of groups of acoustic cycles, each group of acoustic cycles having one or more full acoustic cycles, such that the functional vibrography measures are generated for each group of acoustic cycles, and such that the functional vibrography measures from each group of acoustic cycles are averaged to generate averaged functional vibrography measures.

10. The system according to claim 9 wherein said control and processing circuitry is configured such that the functional vibrography measures corresponding to one or more consecutive image frames are averaged for each selected image line.

11. The system according to claim 9 wherein said control and processing circuitry is configured such that each group of acoustic cycles includes a single full acoustic cycle.

12. The system according to claim 1 wherein said control and processing circuitry is configured to generate the functional vibrography measures by performing a cross-correlation of the sampled interferograms with the in-phase and quadrature sinusoidal signals at the acoustic stimulus frequency, and averaging over multiple A-scan and/or multiple frames for each selected scanning configuration.

13. The system according to claim 1 wherein said control and processing circuitry is further configured to:
receive input from an operator identifying one or more structural features within a B mode image, the B-mode image having been obtained prior to performing step (a); and
select the selected scanning configurations, where vibrography measurements are to be performed, to spatially overlap with at least one of the one or more structural features.

14. The system according to claim 1 wherein said control and processing circuitry is configured to:
identify one or more structural features within a B mode image, the B-mode image having been obtained prior to performing step (a); and
select the selected scanning configurations, where vibrography measurements are to be performed, to spatially overlap with at least one of the one or more structural features.

15. The system according to claim 1 wherein said control and processing system is configured to generate the functional vibrography measures by:
generating a set of primary vibrography measures for each selected scanning configurations; and
processing the set of primary vibrography measures to generate one or more comparative vibrography measures, wherein the one or more comparative vibrography measures generated based on primary vibrography measures corresponding to different image lines.

16. The system according to claim 1 wherein said control and processing circuitry comprises a field programmable logic gate device, wherein said field programmable logic gate device is operably connected to said optical coherence tomography subsystem to receive the A-scan trigger, and wherein said field programmable logic gate device is operatively connected to said scanning subsystem and said acoustic stimulus source for control thereof.

17. A method of synchronizing the operation of an optical coherence tomographic vibrography system, the optical coherence tomographic vibrography system comprising:
an optical coherence tomography subsystem comprising:
a light source;
an interferometer in optical communication with the light source, wherein the interferometer is configured to generate a sample beam and a reference beam; and a detector in optical communication with the interferometer;

a scanning subsystem for scanning the sample beam onto an object within a field of view, wherein the interferometer is configured to interfere the reference beam with scattered laser light that is scattered from the object such that the interfered reference beam and scattered laser light are detected by the detector; and an acoustic stimulus source for generating an acoustic stimulus and directing the acoustic stimulus onto the object, such that the acoustic stimulus generates vibrations within the field of view of the scanning subsystem;

the method comprising:
(a) synchronizing the scanning subsystem with an A-scan trigger associated with the optical coherence tomography subsystem to scan the sample beam according to a plurality of scanning configurations, with at least one A-scan being performed for each scanning configuration;
(b) while performing step (a), performing the following steps for one or more selected scanning configurations that are selected for performing vibrography measurement:
controlling the scanning subsystem to maintain a scan configuration corresponding to the selected scanning configuration for a time duration corresponding to a plurality of A-scans; and
controlling said acoustic stimulus source to generate the acoustic stimulus with a waveform having a frequency that is less than a frequency of the A-scan trigger, the waveform being generated by synchronously incrementing the phase of the acoustic stimulus with each A-scan trigger, with each cycle of the waveform being associated with multiple A-scans, whereby the accumulation and evolution of the acoustic phase during each waveform cycle is controlled according to the A-scan trigger;
(c) sampling signals detected by the detector, thereby obtaining sampled interferograms; and
(d) processing the sampled interferograms from the selected image lines to generate functional vibrography measures.

18. An optical coherence tomographic vibrography system, the system comprising:
an optical coherence tomography subsystem comprising:
a light source;
an interferometer in optical communication with said light source, wherein said interferometer is configured to generate a sample beam and a reference beam; and
a detector in optical communication with said interferometer;
a scanning subsystem for scanning the sample beam onto an object within a field of view, wherein said interferometer is configured to interfere the reference beam with scattered laser light that is scattered from the object, such that the interfered reference beam and scattered laser light are detected by said detector;
an acoustic stimulus source for generating an acoustic stimulus and directing the acoustic stimulus onto the object, such that the acoustic stimulus generates vibrations within the field of view of said scanning subsystem; and
control and processing circuitry operatively coupled to said optical coherence tomography subsystem, said scanning subsystem, said acoustic stimulus source, said control and processing circuitry comprising a processor and a memory, wherein the processor is configured to execute instructions stored in the memory for performing the steps of:
(a) synchronizing said scanning subsystem with an A-scan trigger associated with said optical coherence tomography subsystem, such that the sample beam is scanned according to a plurality of scanning configurations, and such that at least one A-scan is performed for each scanning configuration;
(b) while performing step (a), controlling said scanning subsystem and said acoustic stimulus source such that, at one or more selected scanning configurations that are selected for performing vibrography measurement, said scanning subsystem dwells for a time duration corresponding to a plurality of A-scans, and the acoustic stimulus is generated and phase-locked to the A-scan trigger, such that the phase of the acoustic stimulus is synchronously and incrementally modified with each A-scan of the plurality of A-scans, and such that the accumulation of acoustic phase during each selected scanning configuration is controlled according to the A-scan trigger;
(c) sampling signals detected by said detector, thereby obtaining sampled interferograms; and
(d) processing the sampled interferograms from the selected scanning configurations to generate functional vibrography measures;
wherein said control and processing circuitry is configured to control said scanning subsystem and said acoustic stimulus source such that a plurality of full acoustic cycles are generated for each selected scanning configuration.

19. An optical coherence tomographic vibrography system, the system comprising:
an optical coherence tomography subsystem comprising:
a light source;
an interferometer in optical communication with said light source, wherein said interferometer is configured to generate a sample beam and a reference beam; and
a detector in optical communication with said interferometer;
a scanning subsystem for scanning the sample beam onto an object within a field of view, wherein said interferometer is configured to interfere the reference beam with scattered laser light that is scattered from the object, such that the interfered reference beam and scattered laser light are detected by said detector;
an acoustic stimulus source for generating an acoustic stimulus and directing the acoustic stimulus onto the object, such that the acoustic stimulus generates vibrations within the field of view of said scanning subsystem; and
control and processing circuitry operatively coupled to said optical coherence tomography subsystem, said scanning subsystem, said acoustic stimulus source, said control and processing circuitry comprising a processor and a memory, wherein the processor is configured to execute instructions stored in the memory for performing the steps of:
(a) synchronizing said scanning subsystem with an A-scan trigger associated with said optical coherence tomography subsystem, such that the sample beam is scanned according to a plurality of scanning configurations, and such that at least one A-scan is performed for each scanning configuration;

(b) while performing step (a), controlling said scanning subsystem and said acoustic stimulus source such that, at one or more selected scanning configurations that are selected for performing vibrography measurement, said scanning subsystem dwells for a time duration corresponding to a plurality of A-scans, and the acoustic stimulus is generated and phase-locked to the A-scan trigger, such that the phase of the acoustic stimulus is synchronously and incrementally modified with each A-scan of the plurality of A-scans, and such that the accumulation of acoustic phase during each selected scanning configuration is controlled according to the A-scan trigger;

(c) sampling signals detected by said detector, thereby obtaining sampled interferograms; and (d) processing the sampled interferograms from the selected image lines to generate functional vibrography measures;

wherein said control and processing system is configured to generate the functional vibrography measures by:

generating a set of primary vibrography measures for each selected scanning configuration; and processing the set of primary vibrography measures to generate one or more comparative vibrography measures, wherein the one or more comparative vibrography measures generated based on primary vibrography measures corresponding to different scanning configurations.

* * * * *